United States Patent
Falahee

(10) Patent No.: US 7,182,770 B2
(45) Date of Patent: Feb. 27, 2007

(54) NEEDLE POSITIONING FORCEPS

(75) Inventor: Mark H. Falahee, Ann Arbor, MI (US)

(73) Assignee: Medical Designs, LLC, Ann Arbor, MI (US)

( * ) Notice: Subject to any disclaimer, the term of this patent is extended or adjusted under 35 U.S.C. 154(b) by 522 days.

(21) Appl. No.: 10/268,373

(22) Filed: Oct. 10, 2002

(65) Prior Publication Data

US 2003/0069600 A1   Apr. 10, 2003

Related U.S. Application Data

(60) Provisional application No. 60/328,059, filed on Oct. 10, 2001.

(51) Int. Cl.
*A61B 17/04* (2006.01)
(52) U.S. Cl. .................................. 606/147
(58) Field of Classification Search ........ 606/139–148, 606/151, 157, 174, 205–210, 228
See application file for complete search history.

(56) References Cited

U.S. PATENT DOCUMENTS

| | | | | |
|---|---|---|---|---|
| 3,906,957 A | * | 9/1975 | Weston | ........... 606/174 |
| 3,921,640 A | * | 11/1975 | Freeborn | ........... 606/207 |
| 4,452,246 A | * | 6/1984 | Bader et al. | ........... 606/174 |
| 4,890,610 A | | 1/1990 | Kirwan, Sr. | ........... 606/51 |
| 5,626,606 A | * | 5/1997 | Schellpfeffer | ........... 606/205 |

\* cited by examiner

*Primary Examiner*—Kevin T. Truong
(74) *Attorney, Agent, or Firm*—Gifford, Krass, Groh, Sprinkle, Anderson & Citkowski, PC

(57) ABSTRACT

A hand-held surgical instrument is well-suited to fluoroscopic x-ray imaging. In needle-positioning forceps, an instrument according to the invention preferably exhibits a length of 8 inches or greater, and is constructed substantially from a radiolucent material, thereby enabling a user to navigate the article without being exposed to the beam. The radiolucent material may include a plastic such as a thermoplastic polymer or carbon fiber, and may be presterilized and disposable for one-time use. In the preferred embodiment, the length of the instrument is on the order of 12 inches or thereabouts, and is lordotically shaped for better conformance to patient curvature. The distal tip of the instrument, which is sufficiently strong to reliably grip a needle, may include a needle-dimensioned indent and/or a pair of opposing resilient pads. A radiopaque pointer may be provided to indicate the distal tip, and the pointer may be provided in the form of a removable adhesive strip. A central finger stop or pad may be located between the proximal and distal ends of the instrument, and one or more needle-bending holes may be provided.

12 Claims, 2 Drawing Sheets

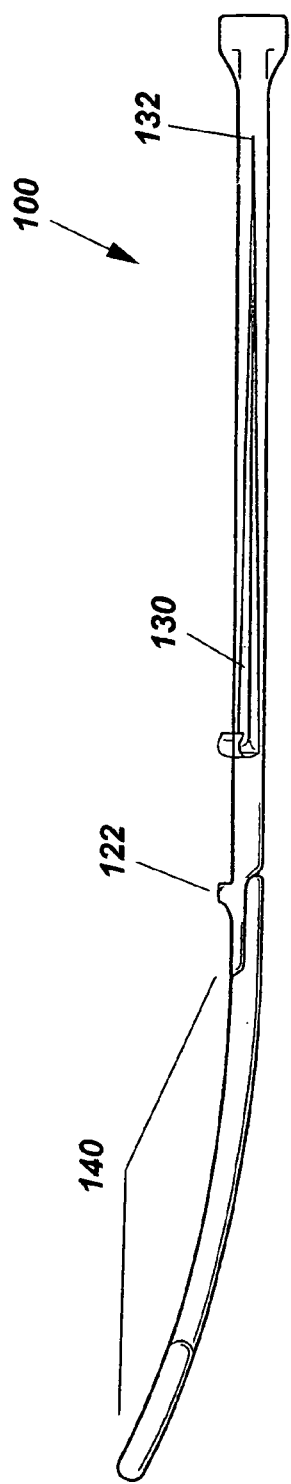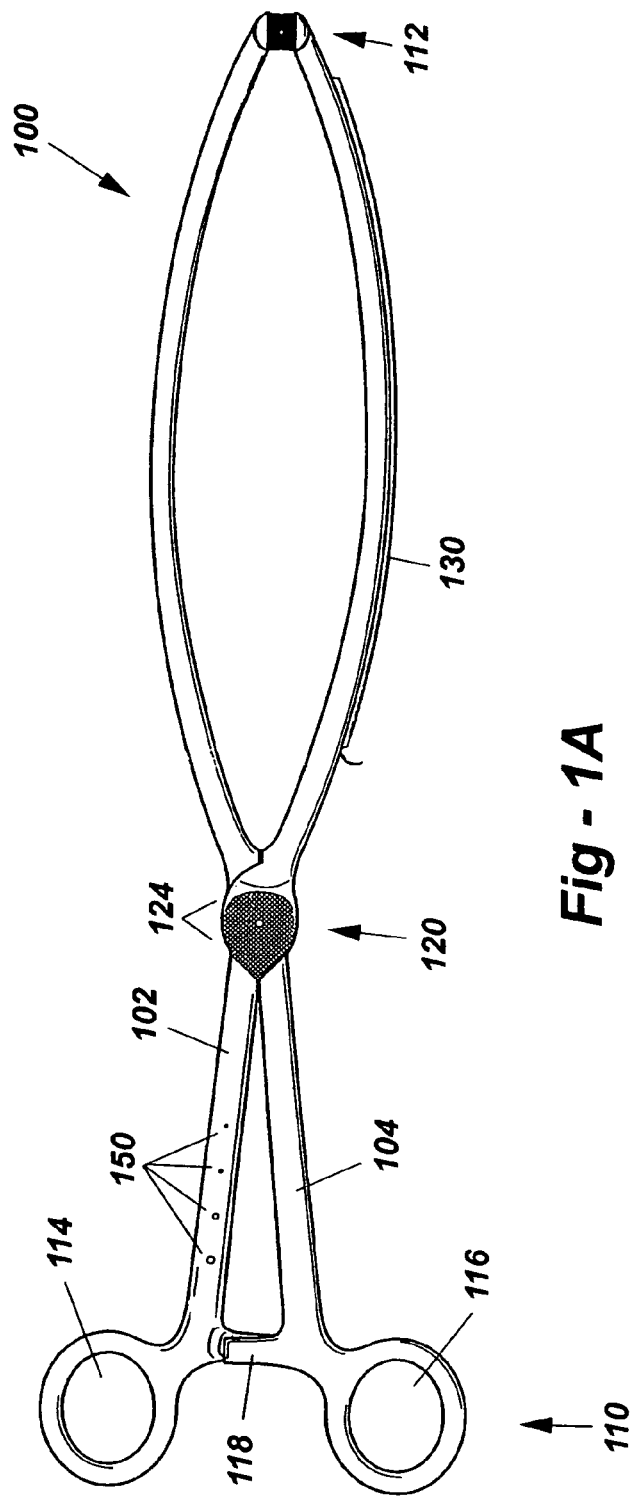

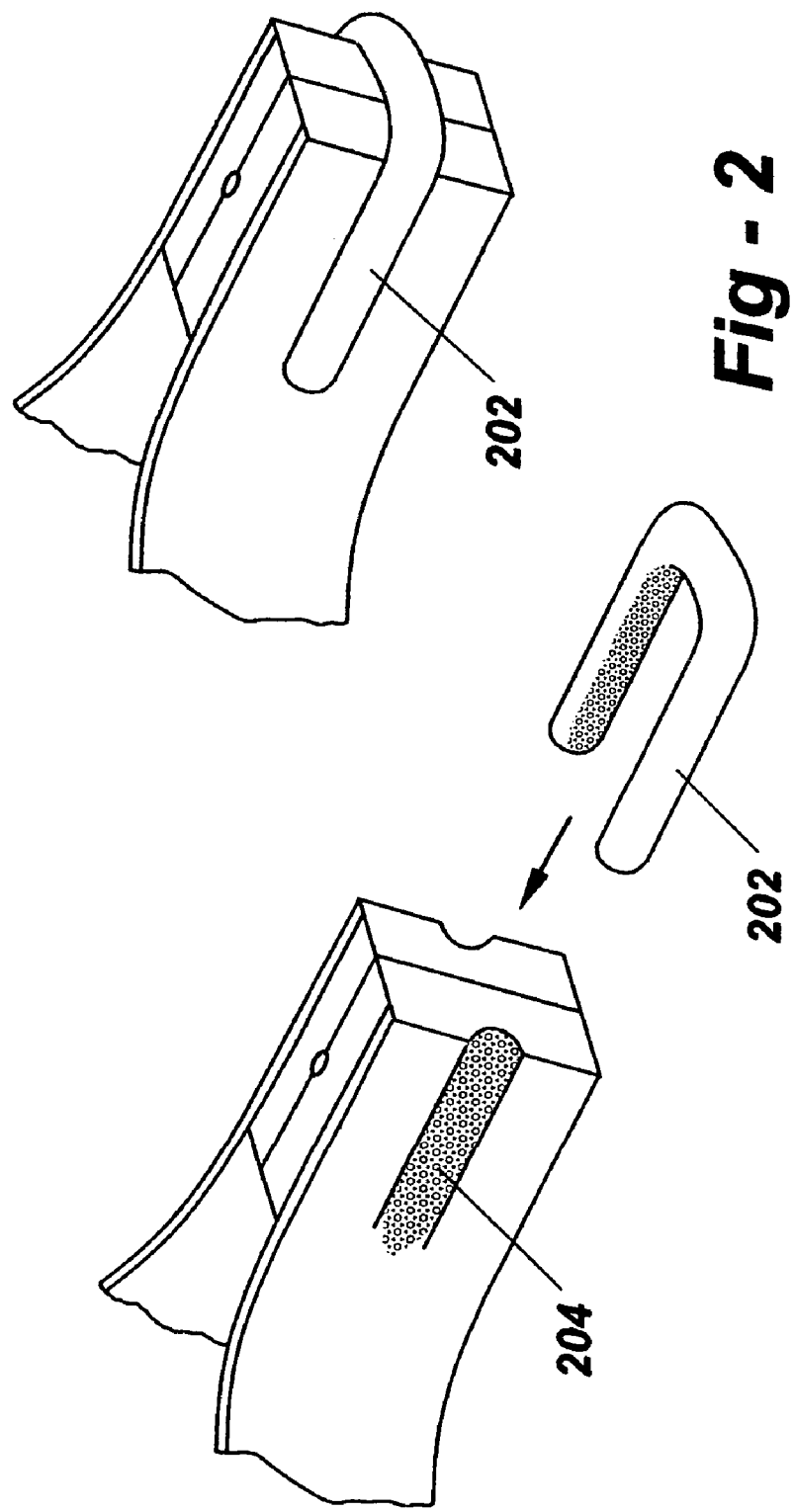

NEEDLE POSITIONING FORCEPS

REFERENCE TO RELATED APPLICATION

This application claims priority from U.S. Provisional Patent Application Ser. No. 60/328,059, filed Oct. 10, 2001, the entire content of which is incorporated herein by reference.

FIELD OF THE INVENTION

This invention relates generally to surgical instruments and, in particular, to a hand-held, substantially radiolucent tool with multiple features for holding and guiding needles and other applications.

BACKGROUND OF THE INVENTION

Minimally invasive surgical (MIS) procedures under arthroscopic or endoscopic magnification and illumination are emerging as alternative, reliable methods of treatment in a variety of cases. With respect to spinal surgery, for example, such operative techniques being used for discectomy, retrieval of herniated disc fragments, stabilization of unstable spinal motion segments, vertebral body biopsy, temporary diagnostic fixation, and epidural access, to name a few. Other orthopedic and non-orthopedic procedures are likewise tending toward MIS approaches.

Typical of these techniques, radiological equipment such as fluoroscopic C-arms are being increasingly deployed to locate radiographic landmarks and markers, guide instruments, and position implants and arthroplastic devices.

Surgical instruments are traditionally manufactured from metals such as aluminum, stainless steel and titanium due to the strength and autoclavability of such materials. However, being radiopaque or X-ray apparent, existing tools often interfere with visualization, causing the surgeon to constantly step away to properly locate devices such as needles. This lengthens the time required to perform the procedure and can interfere with a practitioner's concentration.

Certain types of radiolucent or x-ray invisible devices have been available for some time. For example, radiolucent operating tables, frames and support structures are commonly used, but these are large items. The trend toward radiolucent tools has not evolved rapidly enough with respect to widely used, manually manipulated instruments such as forceps.

SUMMARY OF THE INVENTION

This invention resides in hand-held surgical instruments for use with fluoroscopic x-ray imaging. In a described embodiment taking the form of needle-positioning forceps, an instrument according to the invention includes a manually graspable proximal end and distal end for gripping an article to be navigated. The instrument preferably exhibits a length of 8 inches or greater, and is constructed substantially from a radiolucent material, thereby enabling a user to navigate the article without being exposed to the beam. The radiolucent material may include a plastic such as a thermoplastic polymer or carbon fiber, and may be presterilized and disposable for one-time use.

In the preferred embodiment, the length of the instrument is on the order of 12 inches or thereabouts, and is lordotically shaped for better conformance to patient curvature. The distal tip of the instrument, which is sufficiently strong to reliably grip a needle, may include a needle-dimensioned indent and/or a pair of opposing resilient pads. A radiopaque pointer may be provided to indicate the distal tip, and the pointer may be provided in the form of a removable adhesive strip. A central finger stop or pad may be located between the proximal and distal ends of the instrument, and one or more needle-bending holes may be provided.

BRIEF DESCRIPTION OF THE DRAWINGS

FIG. 1A is a front-view drawing of a needle-positioning forceps according to the invention;

FIG. 1B is a side-view drawing of the needle-positioning forceps of FIG. 1A; and FIG. 2 is a drawing that shows an optional compression clip according to the invention.

DETAILED DESCRIPTION OF THE INVENTION

FIG. 1A is a front-view drawing of a needle-positioning forceps according to the invention, and FIG. 1B is a side-view drawing of the forceps of FIG. 1A. The instrument, shown generally at 100, includes two scissoring elements, 102, 104, which cross in an area 120, and define a length from a proximal portion 110 to a distal portion 112. The proximal portion 110 preferably includes finger-receiving holes 114, 116, and may optionally preferably further include a ratcheting mechanism 118 to enable the physician to maintain a consistent, firm grip on the instrument.

In the preferred embodiment, the instrument is constructed of a radiolucent material so that the instrument will not block or distort an x-ray image, thereby allowing for distancing of the operator hands from the direct x-ray beam. The instrument may be composed of any suitable radiolucent material, such as surgical grade plastic, carbon fiber, thermoplastic polymers, and so forth. Although the instrument may be entirely radiolucent, an indicator tape 130 including a wire or other radiopaque material, may be used on one or more sides of the arms extending from the center 120 to the distal tip 122 to enable the surgeon to visualize the tip during certain procedures. In the preferred embodiment, the tape tapers to a point 132 to better locate the tip of the instrument, while being removable to achieve substantial radiolucent properties for certain procedures. Alternatively, once removed, the peel-off indicator tape may be placed on the patient's skin surface as a temporary indicator.

Further options include a finger positioning area in the region 120, including a stop 122 and/or pad 124 which may be diamond-textured or otherwise roughened. One or more needle-bending holes 150 may be provided enabling the surgeon to bend and/or grasp needles of varying gauge. The distal tip of the instrument may include a needle-dimensioned indent 160 and/or a pair of opposing resilient pads 162 to enhance gripping. In addition, an optional device may be used to keep the distal tip clamped; for example, as shown in FIG. 2, a removable compression clip 202 may engage with a roughened groove 204. The grooves may further ramped so that as the clip is slid deeper, greater compression is applied.

The length of the device overall is preferably on the order of 8 inches or longer, and more preferably on the order of 12 inches, more or less, to enable the surgeon to keep the tool in the beam of the x-ray while the hands of the practitioner are all times substantially outside the beam. Particularly for spine-related procedures, at least the proximal portion includes a lordotic shape, to better conform to the surface of the patient. Although it is anticipated that advanced materials will one day permit radiolucent structures that may be autoclaved, as an alternative, devices according to the invention may be provided as disposable, one-time-use instruments in a pre-packaged, sterile container. In any case, in addition to needle positioning, it will be appreciated by one of skill in the art that the forceps embodiment described herein may be used to position guide wires, biopsy tools, and other items in addition to needles under fluoroscopic x-ray imaging.

I claim:

1. Forceps for use during x-ray beam imaging, comprising:
   a pair of substantially radiolucent scissoring elements, each having a proximal, finger-receiving hole and distal end with an opposing portion of a grip for holding an article to be navigated;
   the scissoring elements crossing at an interconnecting hinge region including an upper finger-positioning area;
   the distance between the finger-receiving holes and the finger-positioning area being substantially less than the distance between the finger-positioning area and the distal end; and
   wherein the scissoring elements each have a length of 8 inches or greater, enabling a user to navigate the article without being exposed to the x-ray beam.

2. The forceps of claim 1, wherein the length of the scissoring elements are 12 inches or thereabouts.

3. The forceps of claim 1, wherein the scissoring elements are sufficiently strong to enable the distal end to reliably grip a needle.

4. The forceps of claim 3, wherein the distal end further includes a needle-dimensioned indent.

5. The forceps of claim 3, wherein the distal end further includes a pair of opposing resilient pads.

6. The forceps of claim 1, wherein the radiolucent material includes a plastic, thermopolymer, or carbon fiber.

7. The forceps of claim 1, further including a radiopaque pointer indicating the distal tip.

8. The forceps of claim 7, wherein the pointer is on a removable adhesive strip.

9. The forceps of claim 1, further including a central finger stop or pad associated with the upper finger-positioning area.

10. The forceps of claim 1, further including one or more needle-bending holes.

11. The forceps of claim 1, wherein the scissoring elements are curved upwardly between the finger-receiving holes and the upper finger-positioning area.

12. The forceps of claim 1, including sterilized packaging for a disposable, one-time use.

* * * * *